(12) United States Patent
Bae et al.

(10) Patent No.: US 10,713,825 B2
(45) Date of Patent: Jul. 14, 2020

(54) MEDICAL IMAGE RECONSTRUCTION DEVICE AND METHOD EMPHASIZING DEPTH INFORMATION

(71) Applicants: VATECH Co., Ltd., Gyeonggi-do (KR); VATECH EWOO Holdings Co., Ltd., Gyeonggi-do (KR)

(72) Inventors: Woong Bae, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 133 days.

(21) Appl. No.: 15/766,763

(22) PCT Filed: Oct. 10, 2016

(86) PCT No.: PCT/KR2016/011325
§ 371 (c)(1),
(2) Date: Apr. 6, 2018

(87) PCT Pub. No.: WO2017/061843
PCT Pub. Date: Apr. 13, 2017

(65) Prior Publication Data
US 2019/0087987 A1 Mar. 21, 2019

(30) Foreign Application Priority Data
Oct. 8, 2015 (KR) .................. 10-2015-0141382

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/14* (2013.01); *A61B 6/501* (2013.01);
(Continued)

(58) Field of Classification Search
CPC ......... G06T 11/008; A61B 6/032; A61B 6/14; A61B 6/501; A61B 6/52223
See application file for complete search history.

(56) References Cited

U.S. PATENT DOCUMENTS

2006/0056673 A1 3/2006 Dehmeshki
2006/0083417 A1 4/2006 Dehmeshki
(Continued)

FOREIGN PATENT DOCUMENTS

EP 2833316 A1 2/2015
JP 2001-204725 A 7/2001
(Continued)

OTHER PUBLICATIONS

European Patent Office, European Search Report of corresponding EP Patent Application No. 16853959.1, dated Jun. 7, 2019.

*Primary Examiner* — Kim Y Vu
*Assistant Examiner* — Molly Delaney
(74) *Attorney, Agent, or Firm* — IP Legal Services, LLC

(57) ABSTRACT

A medical image processing device is disclosed. The disclosed medical image processing device may include: an input interface through which a depth adjusting command is input from a user; an image processor and controller generating a two-dimensional reconstruction image by overlapping a part or all of CT image data in a view direction, and changing a contrast of at least a part of the two-dimensional reconstruction image according to the depth adjusting command; and a display part displaying the two-dimensional reconstruction image.

5 Claims, 14 Drawing Sheets

(51) Int. Cl.
  *A61B 6/14* (2006.01)
  *A61B 6/00* (2006.01)
  *G06T 7/00* (2017.01)
  *A61B 6/02* (2006.01)
  *G06T 11/60* (2006.01)

(52) U.S. Cl.
  CPC .......... *A61B 6/5223* (2013.01); *G06T 7/0012* (2013.01); *A61B 6/025* (2013.01); *G06T 11/60* (2013.01); *G06T 2207/10081* (2013.01); *G06T 2207/20021* (2013.01); *G06T 2207/20076* (2013.01); *G06T 2207/30004* (2013.01); *G06T 2210/41* (2013.01)

(56) References Cited

U.S. PATENT DOCUMENTS

| | | | |
|---|---|---|---|
| 2009/0060309 A1* | 3/2009 | Tsujii | G06T 15/08 382/131 |
| 2009/0310845 A1* | 12/2009 | Ogawa | A61B 6/14 382/132 |
| 2013/0004048 A1 | 1/2013 | Tsujii et al. | |
| 2014/0009573 A1 | 1/2014 | Fujita et al. | |
| 2015/0036790 A1 | 2/2015 | Zoccatelli | |
| 2016/0148399 A1* | 5/2016 | Kim | G06T 19/00 382/131 |
| 2016/0367210 A1 | 12/2016 | Gkanatsios et al. | |

FOREIGN PATENT DOCUMENTS

| | | |
|---|---|---|
| JP | 2001-212135 A | 8/2001 |
| KR | 10-2007-0083645 A | 8/2007 |
| KR | 10-2013-0136519 A | 12/2013 |
| WO | 2015/130916 A1 | 9/2015 |

* cited by examiner

| 1.0 | 1.0 | 1.0 | 1.0 | 1.0 | 1.0 | 1.0 | 1.0 |
|-----|-----|-----|-----|-----|-----|-----|-----|
| 1.0 | 1.7 | 1.0 | 1.0 | 1.0 | 1.0 | 1.0 | 1.0 |
| 1.0 | 1.0 | 2.0 | 2.0 | 2.0 | 2.0 | 1.0 | 1.0 |
| 1.0 | 1.0 | 1.2 | 2.0 | 2.0 | 1.2 | 1.0 | 1.0 |
| 1.0 | 1.0 | 1.0 | 2.0 | 2.0 | 1.0 | 1.0 | 1.0 |
| 1.0 | 1.0 | 1.0 | 1.7 | 1.7 | 1.0 | 1.0 | 1.0 |
| 1.0 | 1.0 | 1.0 | 1.0 | 1.7 | 1.7 | 1.0 | 1.0 |
| 1.0 | 1.0 | 1.0 | 1.0 | 1.0 | 1.0 | 1.0 | 1.0 |

FIG. 12

| 10 | 10 | 10 | 10 | 10 | 10 | 10 | 10 |
|----|----|----|----|----|----|----|----|
| 10 | 105 | 10 | 10 | 10 | 10 | 10 | 10 |
| 10 | 10 | 160 | 250 | 160 | 160 | 10 | 10 |
| 10 | 10 | 110 | 250 | 250 | 15 | 10 | 10 |
| 10 | 105 | 105 | 250 | 250 | 105 | 10 | 10 |
| 105 | 105 | 105 | 200 | 200 | 105 | 105 | 10 |
| 10 | 15 | 15 | 15 | 110 | 110 | 10 | 10 |
| 10 | 10 | 10 | 10 | 10 | 10 | 10 | 10 |

| 10 | 10 | 10 | 10 | 10 | 10 | 10 | 10 |
|----|----|----|----|----|----|----|----|
| 10 | 105 | 10 | 10 | 10 | 10 | 10 | 10 |
| 10 | 10 | 192 | 500 | 192 | 192 | 10 | 10 |
| 10 | 10 | 220 | 500 | 500 | 15 | 10 | 10 |
| 10 | 210 | 210 | 500 | 500 | 210 | 10 | 10 |
| 210 | 210 | 210 | 400 | 400 | 210 | 210 | 10 |
| 10 | 18 | 18 | 18 | 132 | 132 | 10 | 10 |
| 10 | 10 | 10 | 10 | 10 | 10 | 10 | 10 |

| | | | | | | | |
|---|---|---|---|---|---|---|---|
| 10 | 10 | 10 | 10 | 10 | 10 | 10 | 10 |
| 10 | 178.5 | 10 | 10 | 10 | 10 | 10 | 10 |
| 10 | 10 | 320 | 500 | 320 | 320 | 10 | 10 |
| 10 | 10 | 132 | 500 | 500 | 18 | 10 | 10 |
| 10 | 105 | 105 | 500 | 500 | 105 | 10 | 10 |
| 105 | 105 | 105 | 340 | 340 | 105 | 105 | 10 |
| 10 | 15 | 15 | 15 | 187 | 187 | 10 | 10 |
| 10 | 10 | 10 | 10 | 10 | 10 | 10 | 10 |

1400

(a)

(b)

MEDICAL IMAGE RECONSTRUCTION DEVICE AND METHOD EMPHASIZING DEPTH INFORMATION

CROSS REFERENCE TO RELATED APPLICATIONS

This application is a National Stage Patent Application of PCT International Patent Application No. PCT/KR2016/011325 (filed on Oct. 10, 2016) under 35 U.S.C. § 371, which claims priority to Korean Patent Application No. 10-2015-0141382 (filed on Oct. 8, 2015), the teachings of which are incorporated herein in their entireties by reference.

TECHNICAL FIELD

The present invention relates to a method of processing a medical image. More particularly, the present invention relates to a device and method of reconstructing a medical image by emphasizing depth information of the medical image.

BACKGROUND ART

It is generally known that a method for reconstructing a cephalometric image or a panoramic image from a CT data obtained by Computed Tomography with combining the CT data. According to the method, a two-dimensional image such as a cephalometric image is forted by overlapping each slice image of the obtained three-dimensional CT image in a view direction to be seen. There is a limit on representing depth information of a three-dimensional subject by using the two-dimensional image formed by the method since the image is obtained by combining slice images.

Accordingly, in order to increase the utility of a cephalometric image or panoramic image formed by using CT data, research of providing depth resolution information for the same has been conducted. However, according to the research results so far, as a depth resolution increases in a two-dimensional image, the image more becomes a CT image so that it can cause a sense of difference or a confusion may. In addition, conventional methods of emphasizing depth information of a two-dimensional image are performed by identifying depth information of a subject in CT data and processing based thereon, thus it takes long time to identify the corresponding CT slice. For the above reason, the conventional methods of increasing a depth resolution of a two-dimensional image are actually not useful to medical diagnosis.

Accordingly, an image processing method capable of decreasing the sense of difference and the probability of causing confusion in a two-dimensional image and of emphasizing depth resolution information in the two-dimensional image is required.

DISCLOSURE

Technical Problem

An object of the present invention is to provide a device and method forming a two-dimensional image emphasizing depth resolution information capable of providing meaningful depth resolution with reduced possibility of causing the sense of difference and the confusion.

Another object of the present invention is to provide a device and method of forming a two-dimensional image emphasizing a contrast of a region of interest from a subject.

Still another object of the present invention is to a device and method of forming an image emphasizing depth resolution information so that depth information of a subject is rapidly identified.

The objectives of the present invention are not limited to those mentioned above. Other objectives and advantages of the present invention which are not disclosed will be understood from the following description, and it will be apparent with reference to the embodiments of the present invention.

Technical Solution

According to embodiments of the present invention, there is provided a medical image processing device. The medical image processing device may include an input interface which is configured to input a depth adjusting command from an user; an image processing and control unit which is configured to generate a two-dimensional reconstruction image by overlapping a part or all of CT image data in a view direction, and change a contrast of at least a part of the two-dimensional reconstruction image according to the depth adjusting command; and a display unit configured to display the two-dimensional reconstruction image.

In one embodiment, the two-dimensional reconstruction image may be a cephalometric image or panoramic image.

In one embodiment, the image processing and control unit may set a plurality of sections in the CT image data according to the view direction, generate a weight map for each of the plurality of sections, and change a contrast of at least a part of the two-dimensional reconstruction image based on a weight map of a selected section according to the depth adjusting command.

According to embodiments of the present invention, there is provided a medical image processing method. The medical image processing method may include: step (a) of generating a two-dimensional reconstruction image by overlapping a part or all of CT image data in a view direction; and step (b) of changing a contrast of at least a part of the two-dimensional reconstruction image according to a depth adjusting command input from a user, and displaying the changed two-dimensional reconstruction image.

In one embodiment, the two-dimensional reconstruction image may be a cephalometric image or panoramic image.

In one embodiment, the step (a) may include setting a plurality of sections in the CT image data in the view direction, and generating a weight map for each of the plurality of sections.

In one embodiment, the step (b) may include changing a contrast of at least a part of the two-dimensional reconstruction image based on a weight map of a selected section according to the depth adjusting command.

Advantageous Effects

According to embodiments of the present invention, a two-dimensional image through which the sense of difference and the probability of causing confusion can be decreased, and useful depth resolution information and an emphasized contrast can be provided.

DESCRIPTION OF DRAWINGS

FIG. 11 is a view showing a weight map for a second section.

FIG. 12 is a view showing a two-dimensional image that is reconstructed by overlapping a first layer image of FIG. 6 with a second layer image of FIG. 7.

FIG. 13 is a view showing a result in which a weight map for a first section of FIG. 10 is applied to a two-dimensional reconstruction image of FIG. 12 when a first section is selected.

FIG. 14 is a view showing a result in which a weight map for a second section of FIG. 11 is applied to a two-dimensional reconstruction image of FIG. 12 when a second section is selected.

MODE FOR INVENTION

The above and other objects, features, and advantages of the invention will become apparent from the detailed description of the following embodiments in conjunction with the accompanying drawings. It should be understood that the present invention is not limited to the following embodiments and may be embodied in different ways, and that the embodiments are given to provide complete disclosure of the invention and to provide a thorough understanding of the invention to those skilled in the art. The scope of the invention is defined only by the claims.

The terminology used herein is for the purpose of describing particular embodiments only and is not intended to be limiting of the invention. As used herein, the singular forms are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. In addition, the terms "module", "part", and "unit" are used to signify a unit that processes at least one function or operation.

In addition, all the terms that are technical, scientific or otherwise agree with the meanings as understood by a person skilled in the art unless defined to the contrary. Common terms as found in dictionaries should be interpreted in the context of the related technical writings not too ideally or impractically unless the present disclosure expressly defines them so.

Hereinafter, embodiments of the present disclosure will be described in detail with reference to the accompanying drawings. However, in the following description, a detailed description of known functions and configurations incorporated herein will be omitted for the purpose of clarity.

Figure 1:
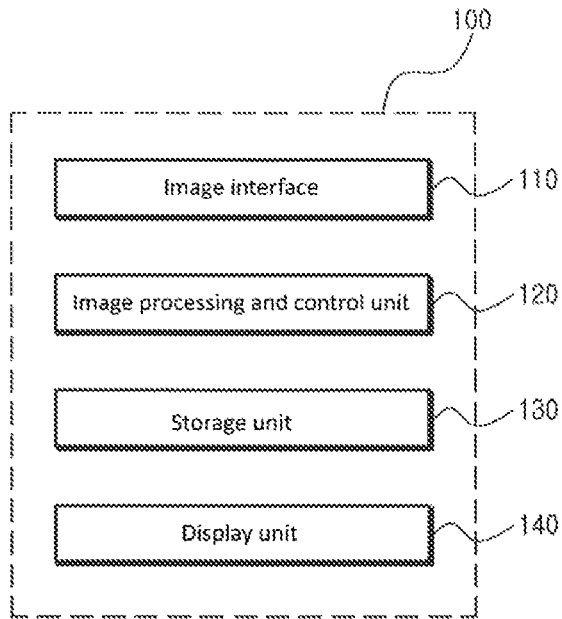
FIG. 1 is a view showing a configuration of an example of a hardware platform for executing a method of emphasizing depth information in a two-dimensional image according to the present invention.

FIG. 1 is a view showing a configuration of an example of a hardware platform for executing a method of emphasizing depth information in a two-dimensional image according to the present invention.

As shown in FIG. 1, an image processing device 100 may include an input interface 110, an image processing and control unit 120), a storage unit 130, and a display unit 140. The input interface 110 may be configured with a hardware or software module for receiving an input of a user command for performing image processing according to various embodiments of the present invention. The input interface 110 may be usefully used for performing various image processing operations by inputting various necessary commands to the image processing and control unit 120 or by indicating a part or all of a displayed image. In one embodiment, the input interface 110 may include a computer keyboard, a keypad, a touchpad, a mouse, etc., but types of the input interface are not limited thereto. For example, the input interface 110 may include a graphic user interface controlled by the above described input devices. The display unit 140 is for displaying various images formed according to various embodiments of the present invention, and may include various display devices such as an LCD display, an LED display, an AMOLED display, a CRT display, etc.

The storage unit 130 may store various types of image data such as three-dimensional CT data obtained by CT photographing a subject, two-dimensional reconstruction image data generated by using three-dimensional CT data, weight map data generated according to various embodiments of the present invention, table mapping data used for generating a weight map, image data of an intermediate result obtained by performing image processing operations according to various embodiments of the present invention, two-dimensional reconstruction image data in which depth information obtained by performing image processing operations according to various embodiments of the present invention is changed, etc. The storage unit 130 may further store a software/firmware required for implementing the image processing and control unit 120. The storage unit 130 may be implemented by a storage medium of any one of a flash memory type, a hard disk type, a multimedia card (MMC), a card type memory (for example, secure digital (SD) card or eXtream digital (XD) card, etc., a random access memory (RAM), a static random access memory (SRAM), a read-only memory (ROM), an electrically erasable programmable read-only memory (EEPROM), a programmable read-only memory (PROM), a magnetic memory, a magnetic disc, an optical disc, etc. However, it will be appreciated by those skilled in the art that the embodiment of the storage unit 130 is not limited thereto.

The image processing and control unit 120 may be configured to perform various image processing operations for obtaining a two-dimensional image in which depth resolution information is emphasized according to various embodiments of the present invention by reading a part or all of three-dimensional CT data from the storage unit 130. The image processing and control unit 120 may be programmed to divide a CT image into a plurality of slice images in a view direction, and to generate a weight map for a plurality of sections set in a view direction for the plurality of slice images. The image processing and control unit 120 may be further programmed to generate a two-dimensional reconstruction image by using a plurality of slice images. The image processing and control unit 120 may be further programmed to generate a two-dimensional reconstruction image in which at least a partial piece of depth information is changed by processing at least a part of the two-dimensional reconstruction image based on a weight map or an addition map in response to a depth adjusting command input by a user through the input interface 110. In order to implement the above described image processing operations, the image processing and control unit 120 may be programmed to perform an overlapping process of a plurality of images in a pixel unit or block unit, to perform arithmetic operations such as addition and subtraction of a plurality of images, multiplication and division of pixel values of an image, etc. In one embodiment, the image processing and control unit 120 may be programmed to implement operations of emphasizing an image contrasts, restoring an image, and performing image filtering.

The image processing and control unit 120 may be implemented by using at least one of, in a hardware aspect, application specific integrated circuits (ASICs), digital signal processors (DSPs), digital signal processing devices (DSPDs), programmable logic devices (PLDs), field-programmable gate arrays (FPGAs), processors, controllers, micro-controllers, and microprocessors. The image processing and control unit 120 may be implemented by a firmware/software module capable of being executed in the above hardware platform. Herein, the firmware/software module may be implemented by using one or more software applications written in a proper programming language.

Figure 2:
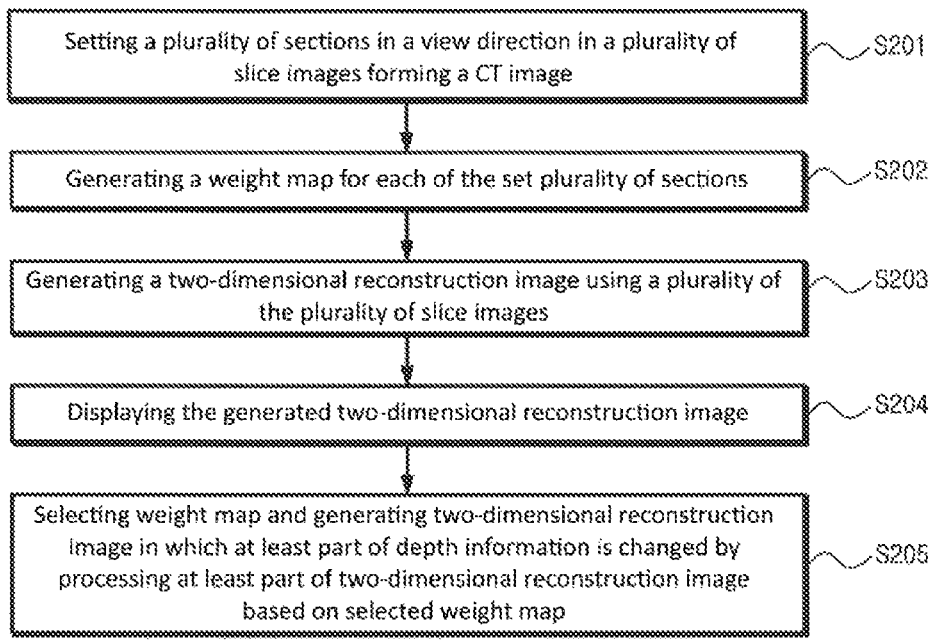
FIG. 2 is a view showing a flowchart of showing an embodiment of a method of emphasizing depth information in a two-dimensional image according to the present invention.

FIG. 2 is a view showing a flowchart of an embodiment of a method of emphasizing depth information in a two-dimensional image according to the present invention.

Figure 3:
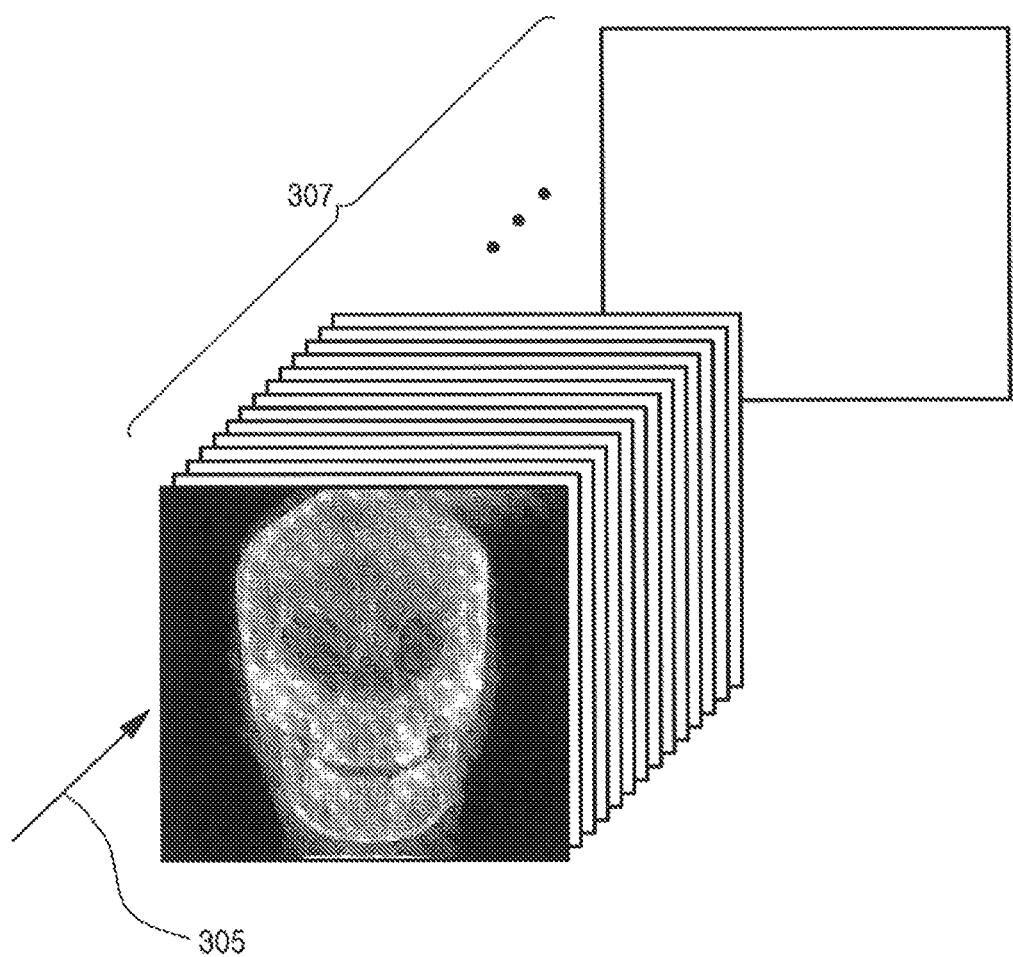
FIG. 3 is a view showing an example of a plurality of slice images of a CT image.
Figure 4:
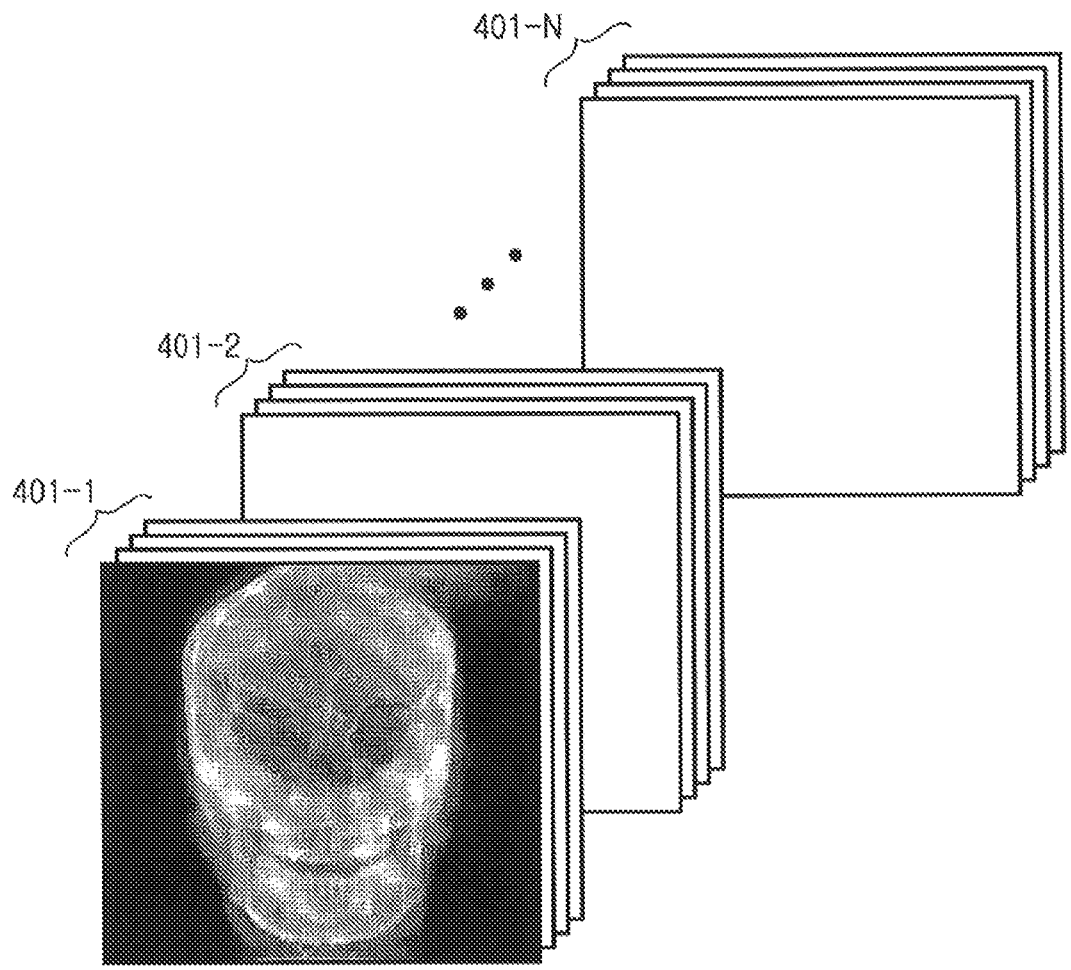
FIG. 4 is a view showing an example of dividing a plurality of slice images of a CT image into a plurality of sections in a direction of a coronal view.

A method of processing a medical image according to an embodiment of the present invention is started by step S201 of setting a plurality of sections in a view direction in a plurality of slice images forming a CT image. FIGS. 3 and 4 are views showing an example of dividing a plurality of slice images 307 of a CT image into a plurality of sections 401-1 to 401-N in a coronal view direction 305. However, in addition to a coronal view direction, the plurality of slice images 307 may be divided into a plurality of sections in a sagittal view direction or in an axial view direction. In the shown embodiment, for example, the plurality of slice images 307 are uniformly divided such that a predetermined number of slice images (for example, four) is included in each section. However, the plurality of slice images 307 may be divided such that a number of slices images which is different from each other is included in each section.

Figure 5:
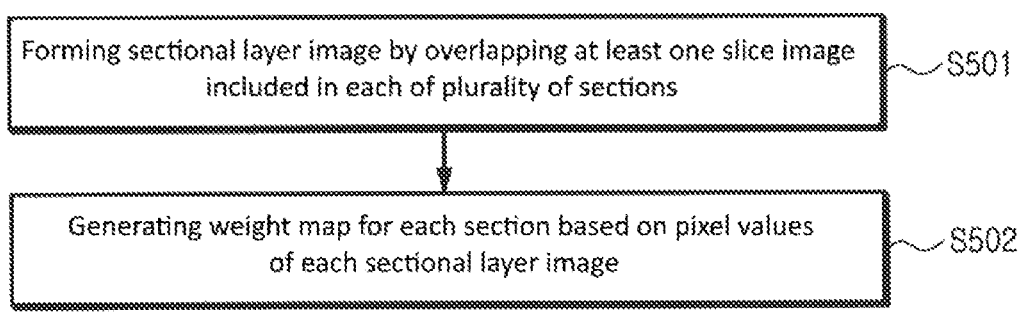
FIG. 5 is a view showing a flowchart of a detailed process of step S202 of generating a weight map in FIG. 2.

In step S202, a weight map is generated for each of the plurality of sections set in step S201. The weight map for each of the plurality of sections may include weight values of respective pixel positions. Hereinafter, referring to FIGS. 5 to 9, step S202 will be described in detail. First, FIG. 5 is a view of a flowchart of a detailed process of step S202 of generating a weight map in FIG. 2.

Figure 6:
FIG. 6 is a view of an example of showing a simplified image having an 8×8 pixel size in a first layer image.
Figure 7:
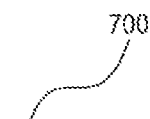
FIG. 7 is a view of an example of showing a simplified image having an 8×8 pixel size in a second layer image.

In step S501, a sectional layer image of a corresponding section is formed by overlapping at least one slice image included in each of the plurality of sections. The sectional layer image may be obtained by overlapping at least one slice image included in each section. In one embodiment, the sectional layer image may be obtained by calculating an average or a weighted average for each pixel in a view direction from at least one slice image included in each section. FIGS. 6 and 7 are views showing examples of simplified images having an 8×8 pixel size as a sectional layer image. Hereinafter, for a convenience of description, it is assumed that a number of sectional layer images is two, and two sectional layer images shown in the examples of FIGS. 6 and 7 are respectively called a first layer image 600 and a second layer image 700.

In step S502, a weight map of the corresponding section is generated based on pixel values of respective sectional layer images formed in step S501. In one embodiment, a weight value for each pixel set for emphasizing each contrast of the formed sectional layer images may be determined as a weight value at the corresponding pixel position in the weight map for the corresponding section. In one embodiment, when the pixel value in the corresponding sectional layer image becomes large, a weight value at the corresponding pixel position in the weight map for the corresponding section may be set to be large. In one embodiment, weight values of the weight map for the corresponding section may be set to be proportional to corresponding pixel values in the corresponding sectional layer image. In one embodiment, a minimum value to a maximum value of pixel values in the corresponding sectional layer image may be identified, for at least one pixel position of the weight map for the corresponding section which corresponds to at least one pixel in the corresponding sectional layer image which has a minimum value, a minimum weight value may be assigned, and for at least one pixel position of the weight map of the corresponding section which corresponds to at least one pixel in the corresponding sectional layer image which has a maximum value, a maximum weight value may be assigned. In one embodiment, for pixel positions of the weight map for the corresponding section which correspond to pixels in the corresponding sectional layer image which have values between the minimum value and the maximum value, values obtained by interpolating based on the minimum weight value and the maximum weight value may be assigned as weight values. A minimum weight value and a maximum weight value may be set to have an arbitrary value for emphasizing a contrast of each sectional layer image. When a difference between the minimum weight value and the maximum weight value becomes large, a contrast and a depth resolution rise. Alternatively, when the difference becomes small, the effect of emphasizing depth information becomes poor. In addition, when the minimum weight value becomes too small, the detail of the image is lost, and when the maximum weight value becomes too large, a resolution of an object with high luminance may be degraded. Accordingly, by considering the above features, the minimum weight value and the maximum weight value may be selected according to the diagnostic purpose. In one embodiment, the minimum weight value may be set to be equal or greater than 0 and equal to or less than 1.0, and the maximum weight value to an arbitrary value equal or greater than 1.0, but the minimum weight value and the maximum weight value are not limited thereto.

As describe above, an example of step S502 of generating a weight map of a corresponding section based on pixel values of respective section layer images has been described. However, in step S502, rather than generating the weight map, an addition map may be generated. For example, when it is assumed that a pixel value in a specific sectional layer image is a in the embodiment described above, and a weight value in a weight map corresponding to the specific sectional layer image is b, a value of a*(b−1) may be set as a weight value in a corresponding addition map.

Figure 8:
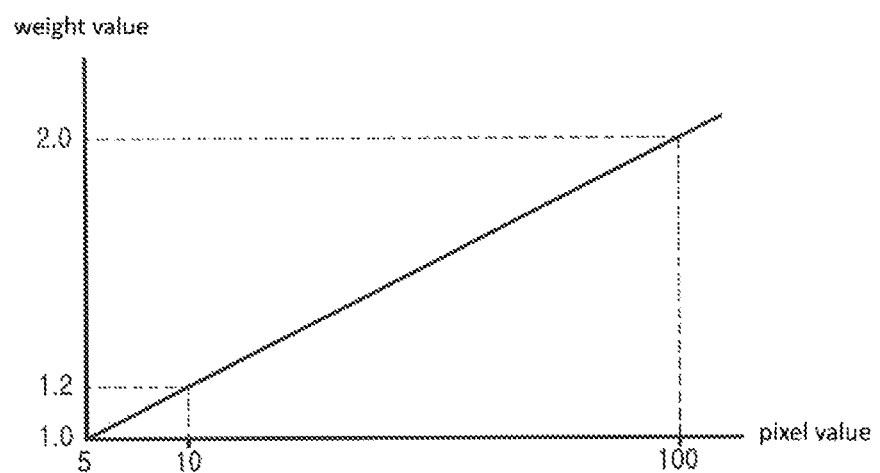
FIG. 8 is a view showing an example of a curve in which pixel values of a first layer image are mapped to weight values of a weight map for a first section.
Figures 9, 10:
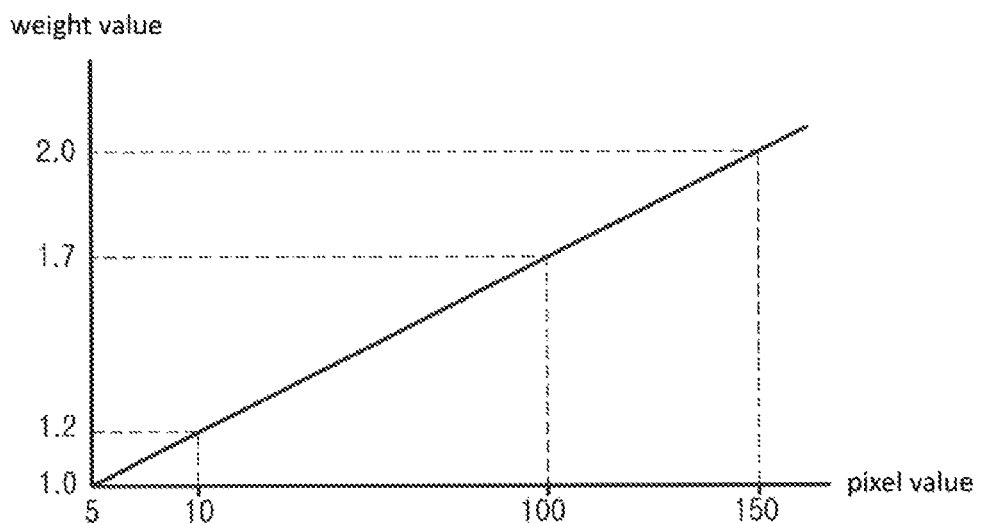
FIG. 9 is a view showing an example of a curve in which pixel values of a second layer image are mapped to weight values of a weight map for a second section.
FIG. 10 is a view showing a weight map for a first section.

Now, a process of generating a weight map is exemplified by using a first layer image 600 and a second layer image 700 shown in FIGS. 6 and 7. In a first layer image 600 of FIG. 6, pixel values of 5, 10, and 100 are present, among them, a minimum pixel value is 5, and a maximum pixel value is 100. In a second layer image 700 of FIG. 7, pixel values of 5, 10, 100, and 150 are present, among them, a minimum pixel value is 5, and a maximum pixel value is 150. In FIGS. 8 and 9, curves in which pixel values in the first and second layer images are respectively mapped to weight values of weight maps of first and second sections. According to an embodiment shown in FIG. 8, 100 that is the maximum pixel value in the first layer image 600 may be mapped to a maximum weight value (it is assumed to be 2.0 in the present embodiment), 5 that is the minimum pixel value may be mapped to a minimum weight value (it is assumed to be 1.0 in the present embodiment), and 10 that is the median pixel value may be mapped to a weight value of about 1.2 that is between the maximum pixel value and the minimum pixel value. According to an embodiment shown in FIG. 9, 150 that is the maximum pixel value in the second layer image 700 may be mapped to a maximum weight value (it is assumed to be 2.0 in the present embodiment), 5 that is the minimum pixel value may be mapped to a minimum weight value (it is assumed to be 1.0 in the present embodiment), and 10 and 100 which are median pixel values may be mapped to weight values of about 1.2 and about 1.7 which are between the maximum pixel value and the minimum pixel value. In one embodiment, the mapping curve of FIGS. 8 and 9 may be implemented in a mapping table. For the purpose of the example, FIGS. 10 and 11 respectively show weight maps 1000 and 1100 for the first and second sections which are generated according to the above described method.

As described above, weight values of a weight map or addition values of an addition map for each of a plurality of sections may be determined as values for emphasizing a contrast of the same image by referencing pixel values of a corresponding sectional layer image. Accordingly, a method of determining weight values or addition values according to the present invention is not limited to the above described embodiments.

Referring again to FIG. 2, in step S203, a two-dimensional reconstruction image is generated by using a plurality of slice images. The two-dimensional reconstruction image reconstructed in the present step may be a cephalometric image or a panoramic image. In one embodiment, a two-dimensional reconstruction image may be generated by overlapping a plurality of slice images in a view direction. In one embodiment, a two-dimensional reconstruction image may be generated by overlapping sectional layer images generated in step S501 in a view direction. For illustrative purposes, a two-dimensional image reconstructed by overlapping the first layer image 600 of FIG. 6 and the second layer image 700 of FIG. 7 is shown in FIG. 12. In step S204, a two-dimensional reconstruction image 1200 generated in step S203 may be displayed.

In step S205, in response to a depth adjusting command input from a user, one weight/addition map determined from weight/addition maps for a plurality of sections is determined, and a two-dimensional reconstruction image in which at least a partial piece of depth information is changed by processing at least a part of the two-dimensional reconstruction image 1200 based on the determined weight/addition map is generated. Herein, the user input may be generated by any one of an operations: designating a position at which the user wants to adjust depth information in the displayed two-dimensional reconstruction image 1200 by using a computer mouse, designating a part at which the user wants to adjust depth information in the displayed two-dimensional reconstruction image 1200 by using a computer mouse as a mask, and selecting a specific section from a plurality of sections by spinning a computer mouse wheel.

When the user input is generated by an operation of designating a position at which the user wants to adjust depth information in the displayed two-dimensional reconstruction image 1200, a section including at least one slice image that represents a characteristic of a subject at the designated position may be selected from a plurality of sections, weight/addition values of a weight/addition map for the selected section may be applied to the two-dimensional reconstruction image 1200 by pixels, thus a two-dimensional reconstruction image in which depth information is changed may be generated. When the user input is generated by an operation of designating a part at which the user wants to adjust depth information in the displayed two-dimensional reconstruction image 1200 as a mask, a section including at least one slice image that represents a characteristic of a subject in the designated mask is selected from a plurality of sections, corresponding weight/addition values of a weight/addition map of the selected section may be applied to designated mask of the two-dimensional reconstruction image 1200 by pixels, thus a two-dimensional reconstruction image in which at least a partial piece of depth information is changed may be generated. When the user input is generated by an operation of, by the user, selecting a specific section from a plurality of sections by spinning a computer mouse wheel, weight/addition values of a weight/addition map for the selected specific section may be applied to the two-dimensional reconstruction image 1200 by pixels, thus a two-dimensional reconstruction image in which depth information is changed may be generated.

In one embodiment, processing of a two-dimensional reconstruction image 1200 in step S205 may include multiplying weight values of the selected weight map by pixel values of the two-dimensional reconstruction image 1200 by pixels. In one embodiment, processing of the two-dimensional reconstruction image 1200 in step S205 may include adding weight values of the selected addition map and pixels values of the two-dimensional reconstruction image 1200 by pixels.

FIG. 13 is a view showing a result in which a weight map 1000 of a first section of FIG. 10 is applied to a two-dimensional reconstruction image 1200 of FIG. 12 when a first section is selected, and FIG. 14 is a view showing a result in which a weight map 1100 of a second section of FIG. 11 is applied to a two-dimensional reconstruction image 1200 of FIG. 12 when a second section is selected. As observed from final result images 1300 and 1400 of FIGS. 13 and 14, it is checked that when the first section is selected, a characteristic of the first layer image 600 is emphasized, and when the second section is selected, a characteristic of the second layer image 700 is emphasized.

Figure 15:
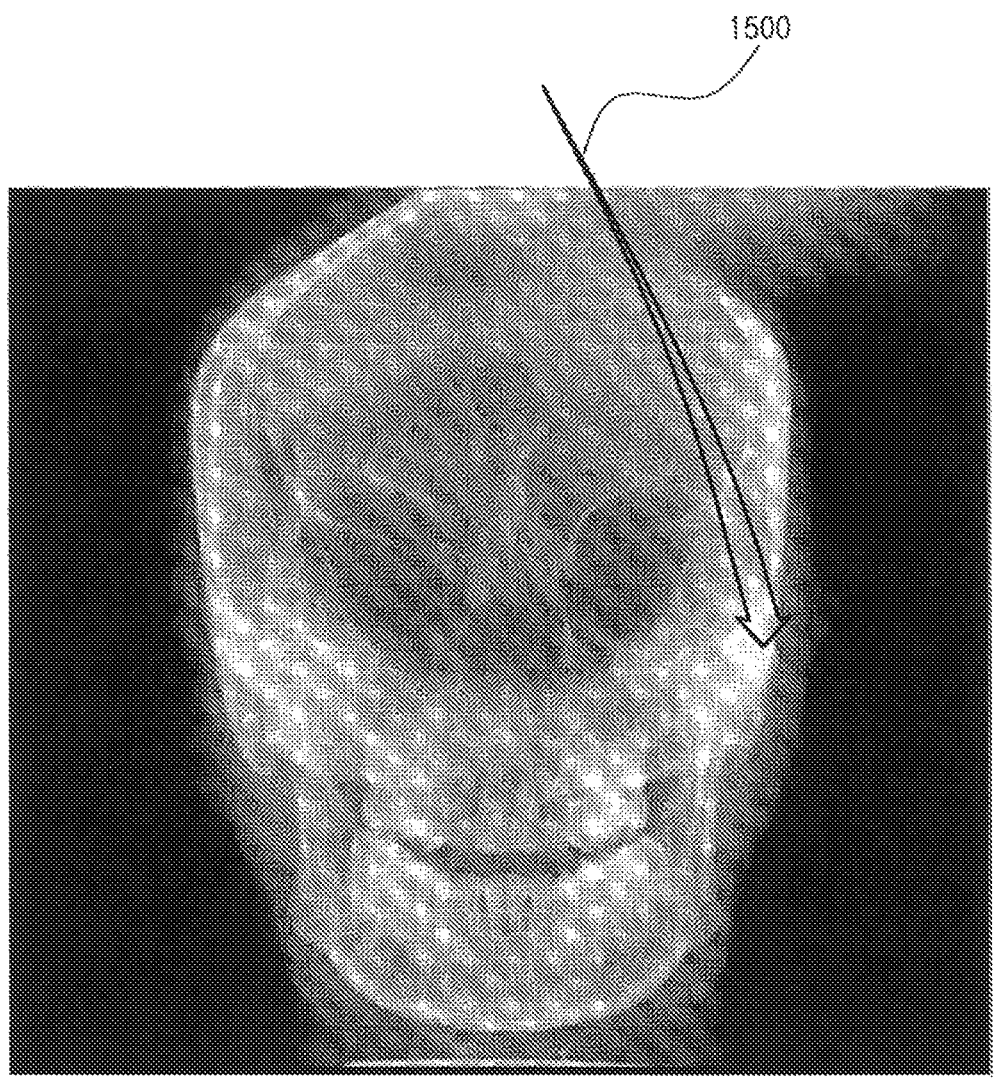
FIG. 15 is a view showing a posterior-anterior (PA) cephalometric image in a direction of a coronal view which is reconstructed by using three-dimensional CT image data obtained from radiographing a head part of a body.
Figure 16:
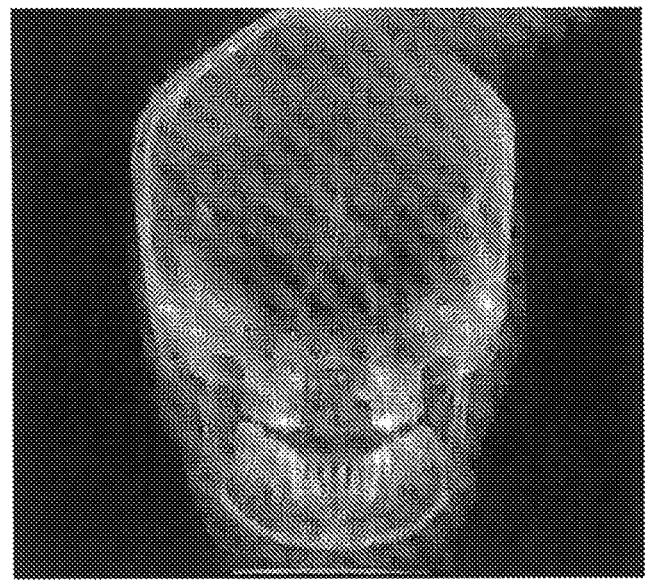
FIGS. 16(a) and 16(b) are views respectively showing result images obtained by performing an image processing according to embodiments of the present invention for the sections showing the characteristics of anterior teeth and posterior teeth among a plurality of sections of three dimensional CT image, and the sections are designated by using a mouse wheel.
Figure 16:
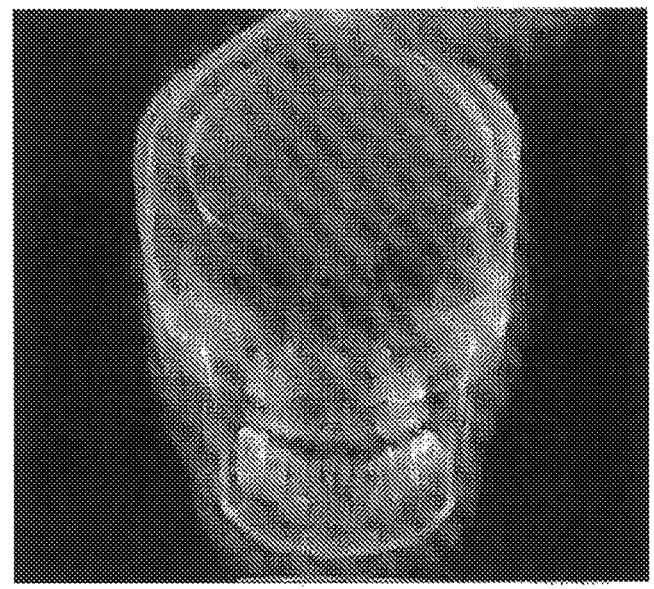
Figure 17:
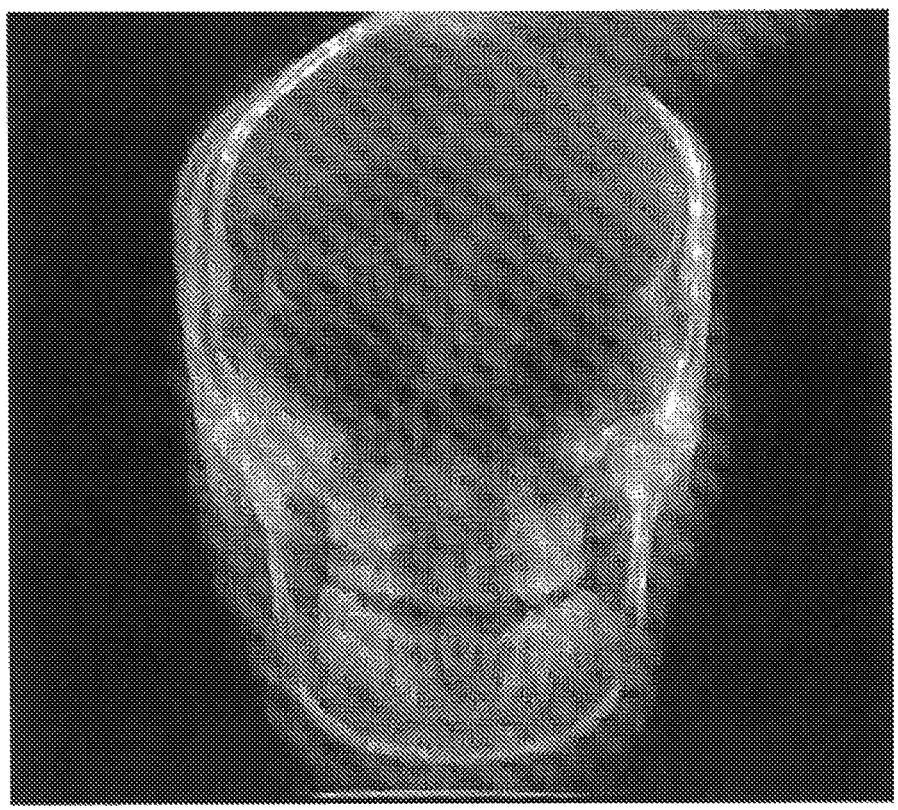
FIG. 17 is a view showing a result image obtained by performing an image processing according to embodiments of the present invention by designating a part indicated by an arrow in FIG. 15 (temporomandibular joint (TMJ)) by using a computer mouse.
Figure 18:
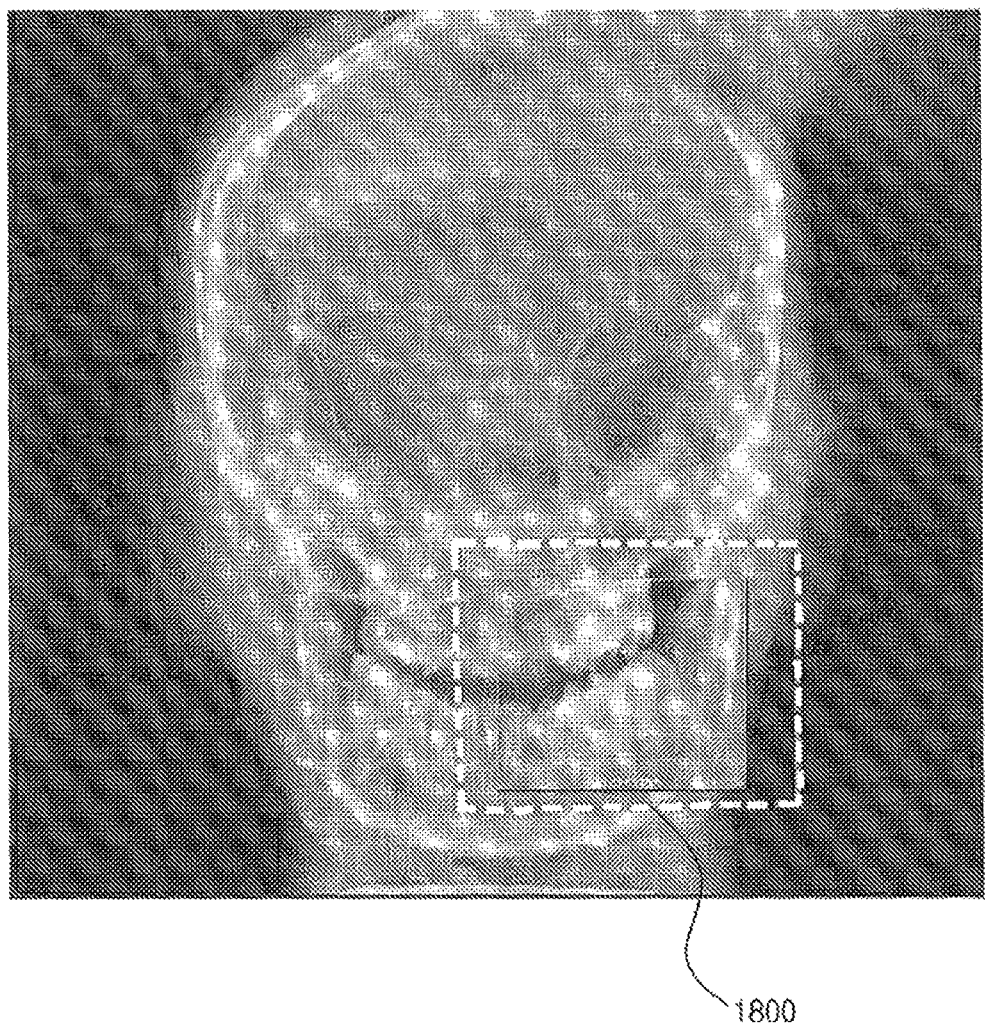
FIG. 18 is a view showing a result image obtained by performing an image processing according to embodiments of the present invention for a mask which is designated by using a computer mouse.

FIG. 15 is a view showing a photo of a coronal view posterior-anterior cephalometric image that is reconstructed by using three-dimensional CT image data obtained by radiographing a head part of a body. FIGS. 16(a) and 16(b) are view respectively showing result images obtained by performing image processing according to embodiment of the present invention by designating sections in which characteristics of anterior teeth and posterior teeth from a plurality of sections of a three-dimensional CT image by spinning a computer mouse wheel. It is checked that characteristics of anterior teeth and posterior teeth shown in photos of FIGS. 16 (a) and 16 (b) are better expressed with high contrast than FIG. 15. FIG. 17 is a view showing a photo of a result image obtained by image processing according to embodiments of the present invention by designating a temporomandibular joint (TMJ) indicated by an arrow 1500 in FIG. 15 by using a computer mouse. It is observed that a contrast of the temporomandibular joint in the photo of FIG. 17 is emphasized more than in the photo of FIG. 15. FIG. 18 is a view showing a photo of a result image obtained by image processing a mask according to embodiments of the present invention which is designated by designating a mask 1800 represented in FIG. 18 as a mask in FIG. 15 by using a computer mouse. Herein, a contrast and a resolution in the mask 1800 is remarkably improved compared to a contrast and a resolution in FIG. 15.

In the embodiments disclosed herein, the arrangement of the components illustrated or the order of the steps may vary depending on the environment and requirements in which the invention is implemented. For example, several components or some steps may be omitted, or several components or some steps may be integrated and executed in one component or in one step. In addition, the arrangement order and connections of some component elements may be changed.

The foregoing exemplary embodiments and advantages are merely exemplary and are not to be construed as limiting. The present invention can be readily applied to other types of apparatuses. Also, the description of the exemplary embodiments is intended to be illustrative, and not to limit the scope of the claims, and many alternatives, modifications, and variations will be apparent to those skilled in the art. Accordingly, the scope of the invention is to be determined solely by the appended claims.

DESCRIPTION OF THE REFERENCE NUMERALS

100: medical image processing device
110: input interface
120: image processing and control unit
130: storage unit
140: display unit
305: view direction
307: slice images
401-1~401-N: sections
600: first layer image
700: second layer image
1000, 1100: weight map
1200: two-dimensional reconstruction image
1300, 1400: final result images
1500: arrow
1800: mask

The invention claimed is:

1. A device for processing a medical image, the device comprising:
    an input interface configured to receive a depth adjusting command from a user;
    an image processing and control unit configured to generate a two-dimensional reconstruction image by overlapping a part or all of CT image data in a view direction, and change a contrast of at least a part of the two-dimensional reconstruction image according to the received depth adjusting command; and
    a display unit displaying the two-dimensional reconstruction image,
    wherein the image processing and control unit sets a plurality of sections in the CT image data along the view direction, generates a weight map for each of the plurality of sections, and changes a contrast of at least a part of the two-dimensional reconstruction image based on the weight map of a selected section according to the depth adjusting command.

2. The device of claim 1, wherein the two-dimensional reconstruction image is a cephalometric image or panoramic image.

3. A method of processing a medical image, the method comprising:
    generating a two-dimensional reconstruction image by overlapping a part or all of slice images created based on CT image data in a view direction and displaying the two-dimensional reconstruction image on a display unit;
    receiving a depth adjusting command from a user through an input interface;
    reproducing the two-dimensional reconstruction image according to the received depth adjusting command by changing a contrast of at least a part of the two-dimensional reconstruction image according to the depth adjusting command input; and
    displaying the reproduced two-dimensional reconstruction image on the display unit.

4. The method of claim 3, wherein the two-dimensional reconstruction image is a cephalometric image or panoramic image.

5. The method of claim 3, wherein at least one weight map is created by grouping the slice images arranging in the view direction into a plurality of sections, forming a sectional image layer of each section by overlapping at least one slice image included in each of the plurality of sections, and generating a weight map for each sectional image layer to have weight values corresponding to pixel values of respective sectional image layer.

* * * * *